(12) United States Patent
Hoover (10) Patent No.: US 6,212,427 B1
(45) Date of Patent: Apr. 3, 2001

(54) HEART RATE VARIABILITY FEEDBACK MONITOR SYSTEM

(75) Inventor: Jan C. Hoover, Bainbridge, WA (US)

(73) Assignee: J&J Engineering, Poulsbo, WA (US)

( * ) Notice: Subject to any disclaimer, the term of this patent is extended or adjusted under 35 U.S.C. 154(b) by 0 days.

(21) Appl. No.: 09/243,230

(22) Filed: Feb. 2, 1999

(51) Int. Cl.⁷ .................................................. A61B 5/04
(52) U.S. Cl. ................................................... 600/515
(58) Field of Search ................................ 600/519, 515, 600/520, 521

(56) References Cited

U.S. PATENT DOCUMENTS

| | | | |
|---|---|---|---|
| 3,938,507 | 2/1976 | Sarnoff et al. | 128/2.06 B |
| 4,256,117 | 3/1981 | Perica et al. | 128/690 |
| 4,489,731 | 12/1984 | Baumberg | 128/690 |
| 4,781,200 | * 11/1988 | Baker | 600/519 |
| 4,883,063 | 11/1989 | Bernard et al. | 128/670 |
| 4,909,260 | 3/1990 | Salem et al. | 128/721 |
| 5,351,695 | 10/1994 | Mills et al. | 128/696 |
| 5,411,031 | * 5/1995 | Yomtov | 600/515 |
| 5,464,021 | 11/1995 | Birnbaum | 128/696 |
| 5,902,250 | * 5/1999 | Verrier et al. | 600/515 |

OTHER PUBLICATIONS

"Heart Rate Variability—Standards of Measurement, Physiological Interpretation, and Clinical Use," Special Report of the *Task Force of the European Soc. of Card. and the North Amer. Soc. Of Pacing and Electrophys.* 93(5):1043–1065, 1996.

Berntson et al., "Heart Rate Variability: Origins, Methods, and Interpretive Caveats," Committee Report, *Psychophys.*, 34:623–648, 1997.

\* cited by examiner

*Primary Examiner*—Scott M. Getzow
(74) *Attorney, Agent, or Firm*—Seed IP Law Group PLLC (57) ABSTRACT

A system monitors surface heart rate variability (HRV) activity of a user and provides appropriate feedback to the user. The HRV feedback monitor is sized and configured to be worn by the user. In the depicted embodiment, heart rate variability is measured with electrodes integrally affixed to a housing of the system. Feedback is typically provided using vibrations of certain duration and repetition. The system operates under various user selectable operational modes. Each operational mode is associated with particular heart rate variability feedback criteria used to determine appropriate feedback for the user. The heart rate variability feedback criteria is related to signal levels and time measurements associated with heart rate variability measured of the user. The depicted embodiment includes a computer interface allowing HRV signal data recorded by the HRV feedback monitor to be sent to a computer system. The computer system is also used to adjust and download desired operational modes into the HRV feedback monitor.

25 Claims, 8 Drawing Sheets

HEART RATE VARIABILITY FEEDBACK MONITOR SYSTEM

TECHNICAL FIELD

The present invention relates to physiological monitoring systems and, more particularly, to a heart rate variability feedback monitor system. The present invention is related to commonly assigned, concurrently filed and U.S. application Ser. No. 09/252,606 for ELECTROMYOGRAPHIC FEEDBACK MONITOR SYSTEM, now issued as U.S. Pat. No. 6,076,011; and U.S. application Ser. No. 09/243,094 for RESPIRATION FEEDBACK MONITOR SYSTEM.

BACKGROUND OF THE INVENTION

Each individual has a heart that beats during any given moment at a certain rate generally measured in beats per minute. The heart rate of each individual, however, is generally not constant. Instead, an individual's heart rate varies typically from beat to beat. Tile variation in heart rate is referred to as Heart Rate Variability (HRV). HRV depends upon moment to moment influences of sympathetic and parasympathetic activity of an individual's body. HRV is integral to an individual's response to a wide range of daily influences, including those due to external environment, and those factors directly associated with an individual including breathing patterns, internal physiology, and psychology. An individual's ability to adapt to these influences is directly related to HRV. Thus, HRV can be an important indicator of an individual's fitness level or health condition.

For instance, impairment of an individual's adaptive abilities may lead to development of cardiac, respiratory and immune disorders. Many disorders typically result in decreased HRV of the individual. Decreased HRV relates to many disorders including hypertension, ventricular arrhythmia, heart disease, including myocardial infarction and congestive heart failure, diabetes, sudden infant death syndrome, chronic fatigue, panic disorder, and impending death caused by these and other disorders. The decrease in HRV in these and other disorders typically is related to a decrease in parasympathetic activity, an increase in sympathetic activity, or a disruption in how these two systems interact with one another.

Many health and fitness conditions could be improved if HRV of an individual was known by the individual throughout the day. Feedback given to an individual based on proper monitoring of HRV could then prompt some type of immediate corrective or therapeutic action by the individual. For instance, corrective or therapeutic action could be applied in areas including heart conditions, diabetes, sudden infant death syndrome, chronic fatigue, panic disorder, and respiration.

Unfortunately, prior art devices which monitor HRV are not conducive for use during normal activities throughout the day and night by individuals. Typically, individuals being monitored by prior art devices must go to a clinic or hospital where an HRV monitor is located. Also, these prior art devices do not provide feedback to individuals being monitored. Other prior art devices have been portable, however, these devices determine only heart rate levels but not HRV. Neither the measurement capabilities nor the feedback criteria involve HRV since only absolute levels of heart rate are of interest with these prior art portable devices. The limited accessibility with the lack of feedback of prior art monitors and the lack of HRV monitoring of other prior art devices does not alert individuals of HRV conditions during their normal activities throughout the day and night.

Thus, opportunities to improve health and fitness conditions of individuals remain unfulfilled.

SUMMARY OF THE INVENTION

The invention overcomes the limitations of the prior art and provides additional benefits by providing a heart rate variability (HRV) feedback monitor system. The HRV feedback monitor allows for expanded accessibility under a wide range of activities. As part of the feedback provided, the HRV feedback monitor furnishes effective feedback that is directly related to areas of concern. The feedback is also discrete in nature. This in addition to other aspects of the invention provides effective, discrete, and timely HRV monitoring and feedback without being overly burdensome. Thus, the invention overcomes the problems and difficulties posed by the prior art systems and provides numerous additional benefits.

Aspects of the invention are directed to an HRV feedback monitor system for a user. An aspect of the invention includes a sensor package sized and configured to be worn by the user. A plurality of electrodes affixed to the sensor package are configured to produce electrical signals based on electrical activity of the user's heart. A vibration output device affixed to the sensor package is configured to transmit a vibration signal perceptible by the user when the output device is activated. A memory, affixed to housing, stores HRV feedback criteria. A processor, affixed to the housing and coupled to the electrodes, the vibration output device and the memory, is configured to receive digital signals associated with the electrical signals produced by the electrodes and to determine HRV based on the digital signals. The processor is configured to transmit an activation signal to activate the vibration output device based on whether the determined HRV satisfies HRV feedback criteria. A user control coupled to the processor allows a user to select an operational mode having particular HRV feedback criteria from a plurality of operational modes under which the processor operates.

In another aspect of the invention, the sensor package is an integral part of a housing. The processor is further configured to adjust the HRV feedback criteria of the selected operational mode based on the determined HRV signals. The operational modes include Percent Time Amplitude Mode, Threshold Amplitude Mode, Media Frequency Mode, Prompted Exercise Mode, or Threshold Shaping Mode. A slave output is electrically coupled to the processor by an electrical cable external to the housing in one aspect and by a wireless communication link in another aspect of the invention.

As a conventional in the field of electrical circuit representation, sizes of electrical components are not drawn to scale and various components are enlarged or reduced to improve drawing legibility. Component details have been abstracted in the Figures to exclude detail such as position of components and precise connections used between components.

DETAILED DESCRIPTION OF THE INVENTION

A feedback monitor, and in particular, an apparatus and corresponding method for a heart rate variability (HRV) feedback monitor system for monitoring heart rate variability of a user's body is described in detail below. In the following description, numerous specific details are provided, such as specific configuration of the apparatus, circuit components, ways of wearing the HRV feedback monitor, HRV criteria used for feedback, etc., to provide a thorough understanding of the embodiments of the invention. One skilled in the relevant art, however, will recognize that the invention can be practiced without one or more of the specific details or with other processes, configurations, hardware, etc. In other instances, well-known structures or operations are not shown or described in detail to avoid obscuring the description of the embodiments.

Each of the circuits whose function and interconnection are described in connection with FIGS. 1–5 and 7–8B is of a type known in the art, and one skilled in the art would be able to use such circuits in the described combination to practice the present invention. The internal details of these particular circuits are not part of, nor critical to, the invention. Therefore, a detailed description of the internal circuit operation is not required. Similarly, each of the steps depicted in FIG. 6 is of a type well known in the art and may itself include a sequence of operations which need not be described herein.

The depicted embodiment of the invention solves problems of prior art monitors that are burdensome to use and do not provide associated feedback based on HRV criteria. The depicted embodiment is lightweight and compact, along with other characteristics, so can be worn if needed throughout the day. Also, the depicted embodiment is simple to operate, which promotes ease of use. Further, the depicted embodiment has a feedback mechanism which is discrete allowing use of the HRV feedback monitor in most situations and environments common to everyday life. Also, the feedback mechanism does not require attention to be directed toward the feedback mechanism while users wait for feedback. The depicted embodiment is far less distracting to users and allows users to better practice the activities of concern. In the depicted embodiment, direct feedback is applied to the region of concern on a user. This dramatically increases the amount of positive feedback to the user by directly associating the feedback stimulus with the region of concern on the user's body. All these features of the depicted embodiment are in sharp contrast to prior art systems that are limited to certain locations, hinder users from practicing activities of concern, and do not provide feedback related to HRV. The depicted embodiment's ease of use and wide range of operating locations give users effective feedback regarding their HRV status resulting in opportunities to improve their health and fitness.

Figure 1:
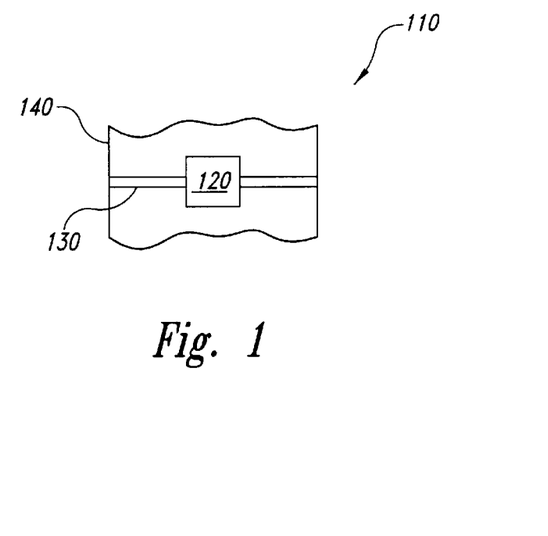
FIG. 1 illustrates an embodiment of the present invention in use.

In order to monitor heart rate variability continually throughout the day, a user ideally should wear an HRV feedback monitor. In this way, the HRV feedback monitor travels with the user rather than the user having to travel to the HRV feedback monitor. The depicted embodiment is small and lightweight enough to be wearable in many positions, locations, and configurations. In the depicted embodiment, the HRV feedback monitor 110 includes a housing 120 and a strap 130 to secure the HRV feedback monitor to a portion of a surface of a user 140 in the vicinity of the user's chest, as shown in FIG. 1. The HRV feedback monitor 110 is worn next to the skin or over the clothes of the user 140 to monitor heart rate variability of the user. The HRV feedback monitor 110 can thus be worn unobtrusively during normal activities. The HRV feedback monitor 110 in other embodiments is secured to the user 140 through the use of clothing. One skilled in the art will recognize that there are many ways to wear the HRV feedback monitor 110 given its small, compact size. The ways depicted in the present embodiments are not intended to limit in any way how the HRV feedback monitor 110 is to be worn.

Figure 2:
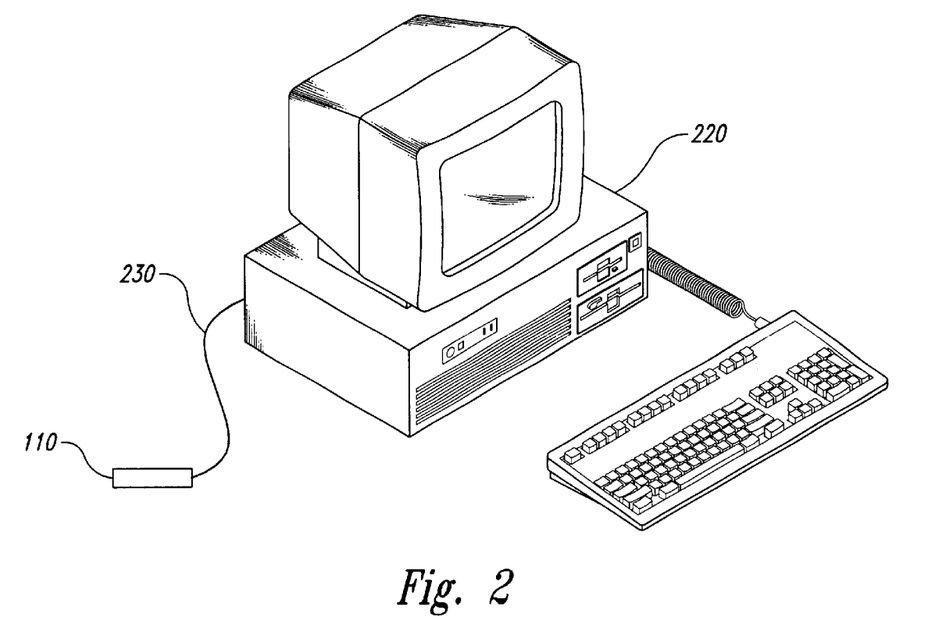
FIG. 2 illustrates the embodiment of FIG. 1 connected to a computer system.

As will be discussed in further detail below, the HRV feedback monitor 110 communicates with a computer system 220 over a computer interface cable 230, as shown in FIG. 2. One end of the computer interface cable 230 has an optical isolation module which provides electrical safety and connection compatibility with a communication port of the computer system 220. Alternative embodiments use other communication links instead of the computer interface cable 230. These other communication links include wireless links or optical fiber links. The computer system 220 is used to program the HRV feedback monitor 110 and also to analyze historical data stored in the HRV feedback monitor related to heart rate variability of a user, such as the user 140. The computer system 220 is thus used to track progress regarding therapeutic intervention or treatment associated with training. Based on the extent of progress that the user experiences, a therapist in the depicted embodiment will adjust or replace criteria used by the HRV feedback monitor 110 to train the user 140 as explained further below. Connection with the computer system 220 via the computer interface cable 230 is typically only an occasional event. Typically, more frequently the user 140 wears the HRV feedback monitor 110 without the HRV feedback monitor being connected to any other type of device.

The computer system 220 executes software that provides several capabilities. The software allows a particular feedback mode to be associated with an HRV feedback monitor control setting and the levels for thresholds and other parameters to be selected for that particular mode. The software can read HRV signal data collected by the computer system 220 from the HRV feedback monitor and cause the data to be displayed such as in graph form on a display of the computer system 220. The software can also store the HRV signal data to appropriate patient/user record files. The software can recall previously stored HRV signal data and produce summary reports of training progress. The software allows visual feedback if the HRV signals are provided to the computer system 220 live by the user 140. This is used to educate the user 140 regarding various feedback vibrations and thresholds for each mode. The software can also provide training information regarding use of the HRV feedback monitor 110.

Figure 3:
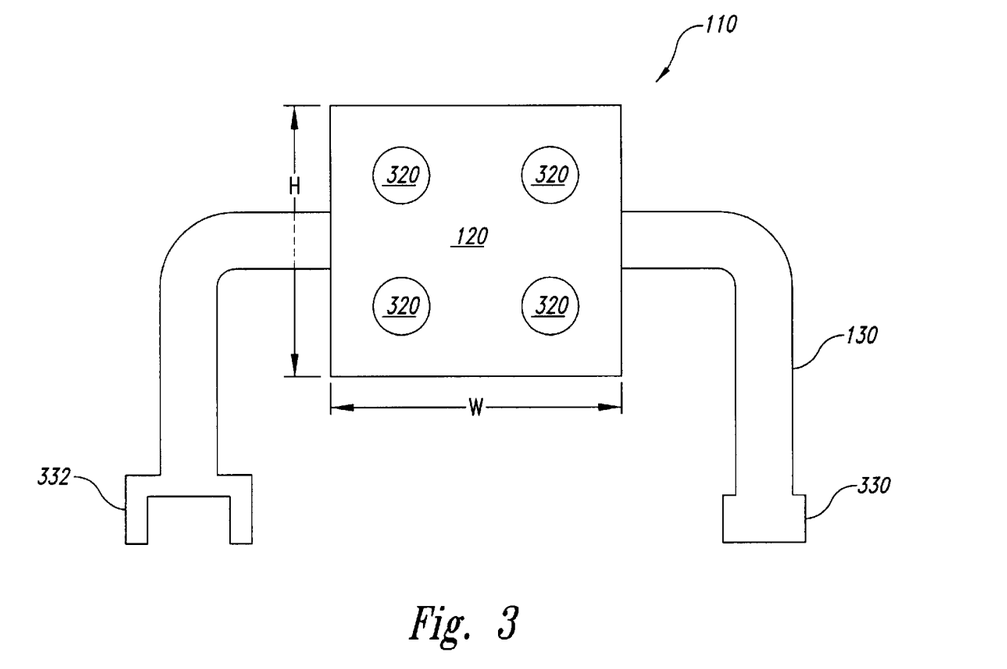
FIG. 3 is a top view of the embodiment of FIG. 1 showing positioning of the electrodes.

The HRV feedback monitor 110 also includes electrodes 320, shown in FIG. 3, that in the depicted embodiment are affixed to the housing 120. The electrodes 320 are positioned in the housing 120 so that as the HRV feedback monitor 110 is secured to a portion of the user 140 with the strap 130 and first portion 330 and second portion 332 of a buckle. The electrodes 320 are positioned on the surface of the portion of the user 140 either against skin or clothing to generate electrical signals based on electrical activity from the user's heart. The HRV feedback monitor 110 uses these electrical signals from the electrodes 320 to determine HRV as described below. In other embodiments, the electrodes 320 are not integrated into the housing 120 of the HRV feedback monitor 110. Instead, the electrodes 320 are detachably connected to the HRV feedback monitor 110 through a signal cable so that the electrodes can be positioned on the user 140 in a location other than where the HRV feedback monitor is positioned. The size of the housing is small, such as about 2 to 4 inches or smaller in height (H on FIG. 3) and about 2 to 8 inches or smaller in width (W on FIG. 3) and about ½ to 2 inches in depth (D on FIG. 3). Preferably, the housing is sized about 2¾ inches in height, about 2¼ inches in width and about ⅝ inches in depth. The housing size greatly contributes to the wearability of the HRV feedback monitor 110.

Figure 4:
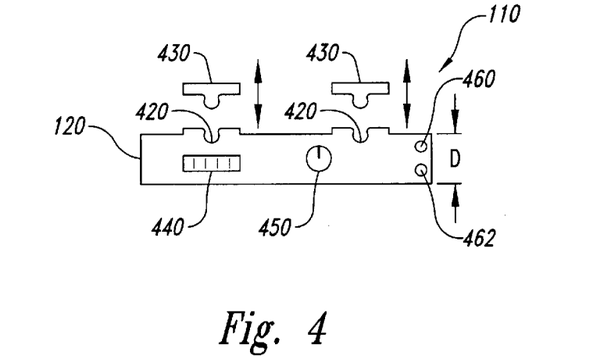
FIG. 4 is a side view of the embodiment of FIG. 1 showing a user control, computer interface connector, and indicator lights.

The HRV feedback monitor 110 also includes electrode snaps 420 configured into the housing 120, as shown in FIG. 4. The electrode snaps 420 receive disposable skin contact electrodes 430 in the depicted embodiment. The electrodes 430 are configured to be a snap fit to, and removable from, the electrode snaps 420. A computer interface cable connector 440 is accessible from the housing 120 so that the computer interface cable 230 can be attached to the HRV feedback monitor 110 for communications to the computer system 220. A user control 450 is positioned on the housing 120 to allow a user to adjust HRV monitoring criteria as discussed further below. In the depicted embodiment the user control 450 is a control knob, but other embodiments have other standard control input devices known in the art such as keypads and switches.

Status indicator 460, typically a red light, and power indicator 462, typically a green light, convey status and power information discussed below to the user 140 about the current condition of the HRV feedback monitor 110. Devices other than lights such as LED displays, audio output devices or other devices known in the art to convey status and power information by other embodiments of the invention.

Figure 5:
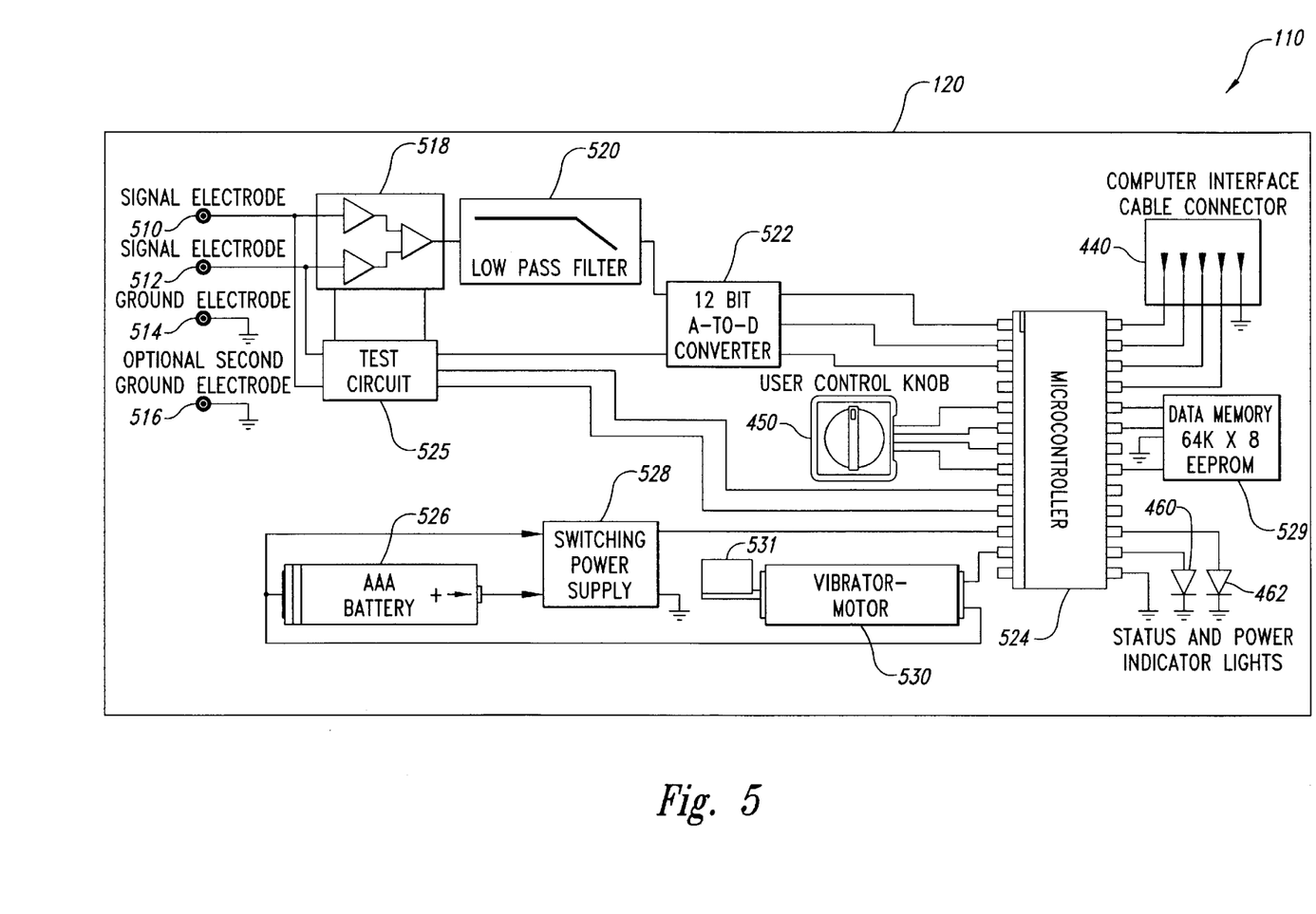
FIG. 5 is a block diagram of circuit details of the embodiment of the present invention of FIG. 1.

Further components of the HRV feedback monitor 110 for the depicted embodiment are shown in FIG. 5. The four electrodes 320 of FIG. 3 are shown in FIG. 5 as signal electrodes 510 and 512, ground electrode 514 and optional second ground electrode 516. The optional second ground electrode 516 is used for mechanical stability and reliability to enhance reliability of the signals being measured. Signal electrodes 510 and 512 are electrically coupled to input amplifier 518. Input amplifier 518 is a differential amplifier which in the depicted embodiment has a gain of 250, self noise equal to 0.5, and common mode rejection equal to 100 dB which are specifications known in the art to describe a differential amplifier. Other embodiments are not limited to these specific specifications of the input amplifier 518.

Input amplifier 518 amplifies the difference of the electrical signals provided by signal electrodes 510 and 512. This difference is then supplied to low pass filter 520 which passes only low frequencies to the 12-bit A to D converter 522. The low pass filter 520 is a 2-pole, 400 Hz filter to remove noise from the signal before being supplied to the A to D converter 522. In other embodiments, filters with other specifications are used appropriately to remove noise. The 12-bit A to D converter 522 then converts the signal provided by the low pass filter in analog form to digital form and passes the digitized signal in a serial manner to the microcontroller 524, also known as a processor. Test circuit 525 is electrically connected to the signal electrodes 510 and 512, the input amplifier 518, the low pass filter 520, the 12 bit A to D converter 522 and microcontroller 524 as shown in FIG. 5. The test circuit 525 performs tests on the various components of the HRV feedback monitor 110 as discussed below.

A power source 526, in the depicted embodiment shown as a AAA battery provides the power for the HRV feedback monitor 110. The battery 526 is electrically coupled to a switching power supply 528 which converts power from the battery 526 to a stable 3.3 volt DC required by the circuitry of the microcontroller 524. Data memory 529 is electronically connected to the microcontroller 524 to furnish data and instructions to the microcontroller. In the depicted embodiment data memory 529 comprises a 64×8 EEPROM, however, any other data and instruction storage device known in the art is contemplated for other embodiments with size being a restriction upon selection. In other embodiments, the microcontroller 524 is monolithically integrated with the data memory 529 on a single integrated circuit chip. In further embodiments, other combinations including some of the input amplifier 518, low pass filter 520, 12 bit converter 522, switching power supply 528, and data memory 529 are monolithically integrated with the microcontroller 524 on a single integrated circuit chip. Additional embodiments locate the microcontroller 524 in a housing separate from where other components such as the input amplifier 518, low pass filter 520, A-to-D converter 522, and data memory 529 are located. In these embodiments the microcontroller 524 communicates with these other components through a data link such as an electrical, optical, or wireless link.

A vibrator-motor 530 with weight 531 is activated by the microcontroller 524 to provide feedback to the user 140 when certain parameters are satisfied to generate a feedback event. These parameters are downloaded into data memory 529 to program the HRV feedback monitor 110. These parameters are selected from parameters including time that measured HRV levels stay above a specified threshold, maximum and minimum threshold levels for HRV levels to exceed and not to exceed, respectively, amount of time since the last feedback event, duration of feedback, percent of overall time that the HRV level is at a certain amplitude, and the amount of standard deviation or corrected standard deviation of the HRV level.

Analysis of HRV level are based either in the time or frequency domains. An extensive scientific discussion of various methods used for HRV analysis in the time and frequency domains is set forth in the following journal articles: "Heart Rate Variability: Standards of Measurement, Physiological Interpretation, and Clinical Use," Circulation, Vol. 93, No. 5, Mar. 1, 1996, pp. 1043–1046, copyrighted by American Heart Association, Inc.; and "Heart rate variability: Origins, methods, and interpretive caveats," Psychophysiology, Vol. 34, 1997, pp. 623–648, Cambridge University Press, Society for Psychophysiological Research (reprints available from Dr. Gary G. Berntson, Dept. of Psychology, Ohio State University, 1885 Neil Avenue, Columbus, Ohio 43210 USA). For the sake of conciseness, only representative methods of HRV measurement in the time and frequency domains are discussed herein. However, further embodiments of the HRV feedback monitor 110 use the additional methods for HRV measurement in time and frequency domains disclosed in the Circulation article. Frequency domain methods include spectral analysis of the measured electrical signals mentioned above from the user's heart measured by the electrodes and recorded in data memory 529 over a given period of time. Spectral analysis focuses on the inherent frequency components involved with heart rate variations. Prior art frequency domain devices have been restricted to clinical environments without providing user feedback. The depicted embodiment brings frequency domain analysis out of the clinical setting to the user's everyday world and joins frequency domain analysis with timely user feedback. The microcontroller 524 analyzes the heart electrical signal data stored in data memory 529 using the techniques and principles of frequency domain analysis to determine current HRV plots related to the user's current HRV and to compare these current HRV plots to model HRV plots or to the user's previous HRV plots. Specifically, the microcontroller 524 generates HRV plots by determining signal amplitude for particular values or ranges of signal frequency and/or collective summations of signal amplitudes for certain ranges of signal frequencies. The microcontroller 524 afterward compares the generated HRV plots to model HRV plots or to the user's previous HRV plots containing similar types of data These comparisons are based on correlation and comparison techniques known in the art. Based on these comparisons, or combined with further conditions discussed below, the HRV feedback monitor 110 applies appropriate feedback.

Frequency domain based feedback is directly tied to HRV and associated physiology. Medical research has determined that the vagus nerve mediates high frequency components of HRV (typically 0.15 to 0.4 Hz or 10–24 cycles per minute). The high frequency components relate to respiratory sinus arrhythmia (RSA). RSA is a normal arrhythmia associated with the vagus nerve and respiration. The components in this high frequency range indicates parasympathetic activity. Both parasympathetic and sympathetic activity influence low frequency components of HRV (typically 0.05 to 0.15 Hz or 3 to 9 cycles per minute). Normal, oscillatory regulation due to hypothalamic and brainstem conditions influence components in this low frequency range. The very low frequency components of HRV (usually less than 0.05 Hz or less than 3 cycles per minute) may relate to temperature regulation or patterns of circulating hormones.

HRV measurements are alternatively based in the time domain. The microcontroller 524 and data memory 529 record the electrical activity of an individual's heart based on voltage level of the electrical signals generated by the electrodes 320 versus time of the voltage level. A resultant graph of the recorded data comprises a series of voltage peaks. Each voltage peak corresponds to a heart beat. Each of these voltage peaks are part of an Rwave. The time interval between successive peaks of two Rwaves is called interbeat interval or heart period. These interbeat intervals each have a duration and are measured in units of time. The duration of the interbeat intervals can vary widely. The distribution of these durations for the interbeat intervals is an index of HRV. These distributions are a way to express HRV plots in the time domain. Ways to characterize this distribution include the standard deviation of the interbeat interval, the standard deviation of the average interbeat interval over some short period of time, the square root of the mean squared differences of successive interbeat intervals, the number of interval differences of successive interbeat intervals greater than a time period (e.g., 50 ms), and the proportion of interbeat intervals greater than a time period (e.g., 50 ms) divided by the total number of intervals. The distributions can also be stored based on percentages of interbeat intervals that have durations in various ranges. These HRV plots in the time domain and related values are either compared to model HRV plots and/or values, or to the user's previous HRV plots and/or values. Based on these comparisons, or combined with further conditions discussed below, the HRV feedback monitor 110 applies an appropriate level of feedback.

The user 140 selects entire sets of parameters associated with particular operational modes having individualized HRV feedback criteria with the user control knob 450 in the form of a rotary switch in the depicted embodiment. In this way, the HRV feedback monitor 110 can be used for different purposes or activity levels. For example, one setting would remind the user 140 not to overwork and another setting would assist the user in relaxing. In the depicted embodiment, a therapist presets these sets of parameters based on clinical information, skill level of the user 140, and appropriate activity for the user 140. The therapist then determines the appropriate setting and downloads several sets of parameters that correspond to different rotary positions of the user control knob 450. Thereafter, the therapist instructs the user 140 regarding the settings of the user control knob 450. For instance, setting 1 could be used during job related activities, setting 2 could be used during sports related activities, setting 3 could be used during resting, etc.

The sets of parameters are downloaded into the HRV feedback monitor 110 from the computer system 220 over the computer interface cable 230 into the HRV feedback monitor. These parameters are used by the microcontroller 524 to analyze the digital signals provided by the A to D converter 522. Depending on the results of the analysis by the microcontroller 524, the data memory 529 stores certain historical data on heart rate variability of the user 140. Typically the therapist indicates which data and statistics are to be stored in the data memory 529 during programming of the HRV feedback monitor 110 when the parameters are downloaded from the computer system 220 into the HRV feedback monitor via the computer interface cable 230.

The parameters stored in data memory 529 may also be modified by the microcontroller 524 directly based upon past activity by the user 140. For example, the user 140 may select with the user control knob 450 feedback criteria so that for the entire time allotted for monitoring, feedback is given for only a certain selected percentage of time. The microcontroller 524 then adjusts and updates the threshold in order that feedback occurs at the selected percentage of time. For example, if the user selects feedback to occur an average of 25% of any given period of time, the microcontroller 524 would take previously recorded heart rate variability and adjust the threshold so that the user was in range 75% of the time and out of range 25% of the time. The microcontroller 524 of the HRV feedback monitor 110 would then give the appropriate amount of feedback. If performance of the user 140 subsequently changes, the microcontroller 524 adjusts the threshold appropriately so that the amount of feedback would still be 25% on average of the overall time for monitoring.

The HRV feedback monitor 110 in the depicted embodiment operates under other operational modes including Percent Time Amplitude, Threshold, Medium Frequency, Prompted Exercise, and Threshold Shaping. Each mode can be operated either with fixed or adaptive thresholds. Adaptive thresholds change based on progress of training. In the Percent Time Amplitude Mode, the microcontroller 524 determines the amount of time that measured HRV is at various values. Preset periods of time are typically generated by moving a preset window of time over the total monitoring time period. The HRV values are averaged for each window of time which is typically an interval of 10 to 500 msec. An expected HRV value is divided into N bins with the number of bins being preselected by the user. For each window of time, the microcontroller 524 assigns a count to the bin corresponding to the average HRV value for that window of time, providing a calculated percentage distribution and showing the percentage of time that HRV averages were at each value. Feedback is given based on calculated percentages associated with certain bins. The thresholds associated with each percentage distribution for each selected bin are independently adjustable.

For the Threshold Mode, when the HRV value either goes above or below a preset threshold over a preset length of time, feedback is given. Also, the repetition or duration of vibration in one embodiment is linear to the amount that the HRV value exceeds a threshold. For example, when the threshold is exceeded by 200%, feedback is given twice as often or lasts twice as long as when the threshold is exceeded by 100%. In the Median Frequency Mode, a median frequency is determined from a spectral analysis by the microcontroller 524 using frequency domain analysis over a given number of samples and a given time window. Median frequency shifts are detected as a percentage change over time or relative to a preset level. Feedback is given when the shift in median frequency exceeds either a percentage or level threshold.

For the Prompted Exercise Mode the user 140 is prompted to begin exercising with a vibration of short duration. The degree of success is then signaled by other vibratory patterns such as vibrations of long duration or multiple vibrations. For example, a patient may go to a therapist. The therapist may determine that the patient can endure a certain level of HRV and then must rest. The therapist determines that this should be repeated for a certain number of times. The therapist then downloads this set of parameters into the data memory 529 and assigns it to switch position 1 of the user control knob 450. Prior to an exercise session, the user then selects switch position number 1 of the user control knob 450. At the beginning of the exercise session, the user 140 receives a single vibration from the vibrator-motor 530 signaling the user to start the exercise. During exercise, when the user 140 exceeds the HRV level threshold, the user then receives two short term vibrations from the vibrator motor 530 signaling the user to relax. After a rest period, the user receives another single vibration from the vibratory motor 530 signaling the user to repeat the exercise. These series of events repeat for the prescribed number of times and then the HRV feedback monitor 110 turns off. Data related to this exercise session is saved in data memory 529 for future reference by the therapist.

The Threshold Shaping Mode provides alternative approaches in tailoring the amount of feedback based on the user's previous performance, established objectives, and the user's individual characteristics. One approach of the Threshold Shaping Mode involves a goal threshold based on a present criteria downloaded by a therapist. The HRV feedback monitor 110 measures a current level of HRV and gives feedback based on the goal threshold and the current measured level of HRV. Next, the HRV feedback monitor 110 computes a median threshold between the current measured level of HRV and the goal threshold. If subsequent HRV levels satisfy the median threshold over a present period of time, the HRV feedback monitor 110 readjusts the median threshold toward the goal threshold, otherwise, the HRV feedback monitor maintains the median threshold and gives feedback. The HRV feedback monitor 110 gradually moves the median threshold toward the goal threshold as subsequent levels of HRV continue to satisfy the median threshold. However, if subsequent levels of HRV fail to satisfy the median threshold over a present period of time, the median threshold is readjusted toward the current level of HRV.

A second approach of the threshold shaping mode involves other feedback modes and procedures including those elaborated for the disclosed embodiments with the other feedback modes and procedures, independent from this second approach, the microcontroller 524 determines an appropriate time to furnish feedback, hereto referred as a feedback event. Under the second method, however, feedback is not actually contingent solely upon a feedback event. Rather, the second approach involves additional conditions to be satisfied before feedback is given.

Under the second approach, the microcontroller 524 additionally determines one or more HRV plots and/or values related to the user's HRV based either in the time or frequency domain. These additional HRV plots and/or values are in addition to HRV plots and/or values that the microcontroller 524 may use to determine feedback events. The microcontroller 524 then compares the additional HRV plots and/or values to model HRV plots and/or values stored in data memory 529. The comparison is based on standard correlation or comparison techniques known in the art. The model HRV plots and/or values are based on either HRV of exceptionally healthy individuals or theoretical ideals. Typically, if HRV of individuals are used, the model HRV plots and/or values of the individuals are measured while the individuals are performing a designated activity such as involved with meditation, sports, recreation, health care, or labor. Based upon the comparison between the additional and model HRV plots and/or values, the microcontroller 524 calculates a trend. This trend indicates whether the user's HRV is improving toward the model HRV. Based on this trend and the feedback events, the microcontroller 524 furnishes an appropriate amount of feedback.

Typically, under this second approach, if the trend indicates that the user's HRV is continuing to approach the model, the microcontroller 524 will furnish feedback only in response to a fraction of the feedback events. This fraction typically ranges from ½ to ¹⁄₁₀ depending upon the user's characteristics and circumstances. Typically, if the user's HRV is staying the same or moving away from the model the fraction will increase usually to 1. The amount of increase of the fraction can be adjusted as part of the threshold criteria downloaded into the data memory 529 according to the user's particular characteristics.

Figure 6A:
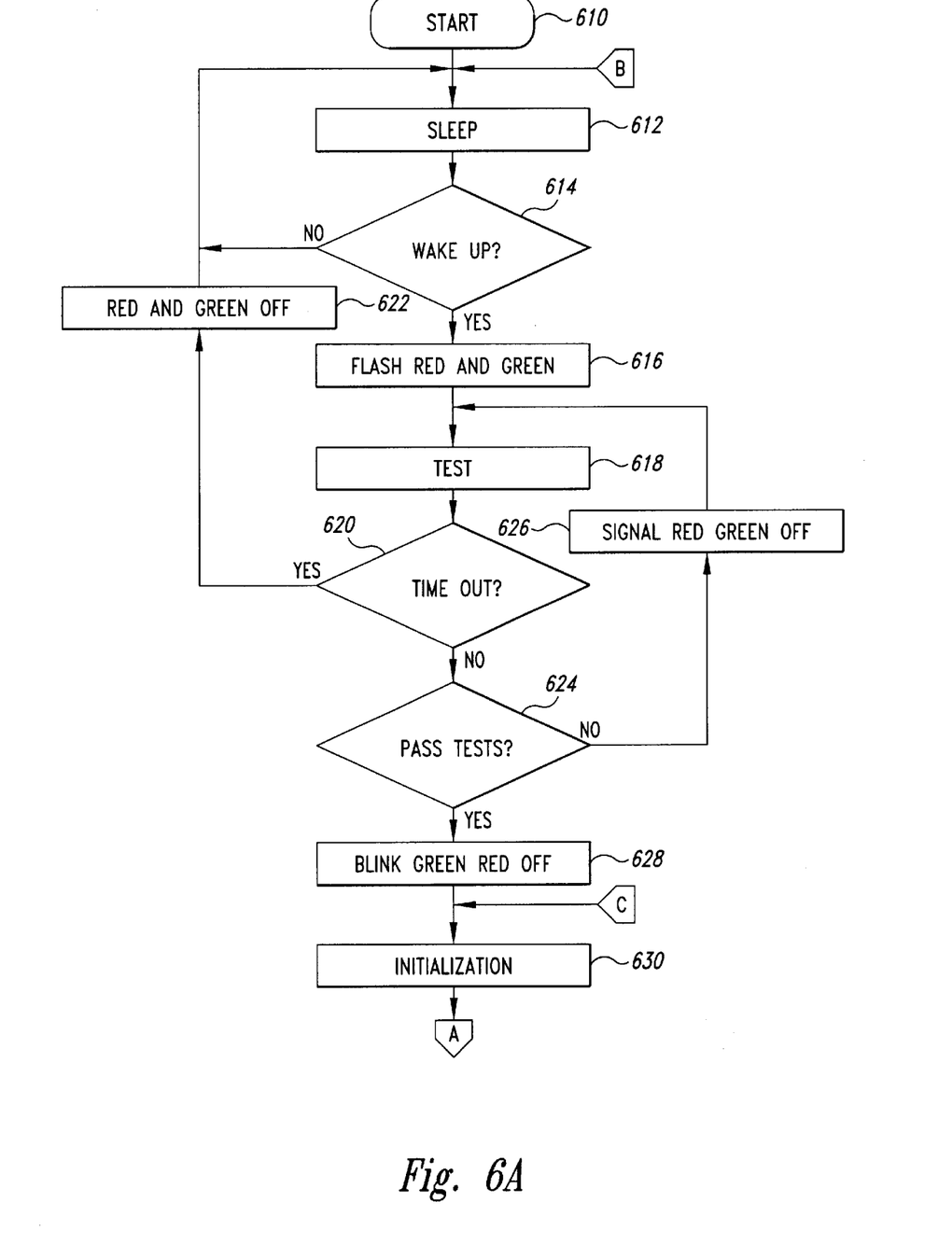
FIGS. 6A and 6B is a flowchart of the process implemented by the microcontroller of the embodiment of FIG. 5.
Figure 6B:
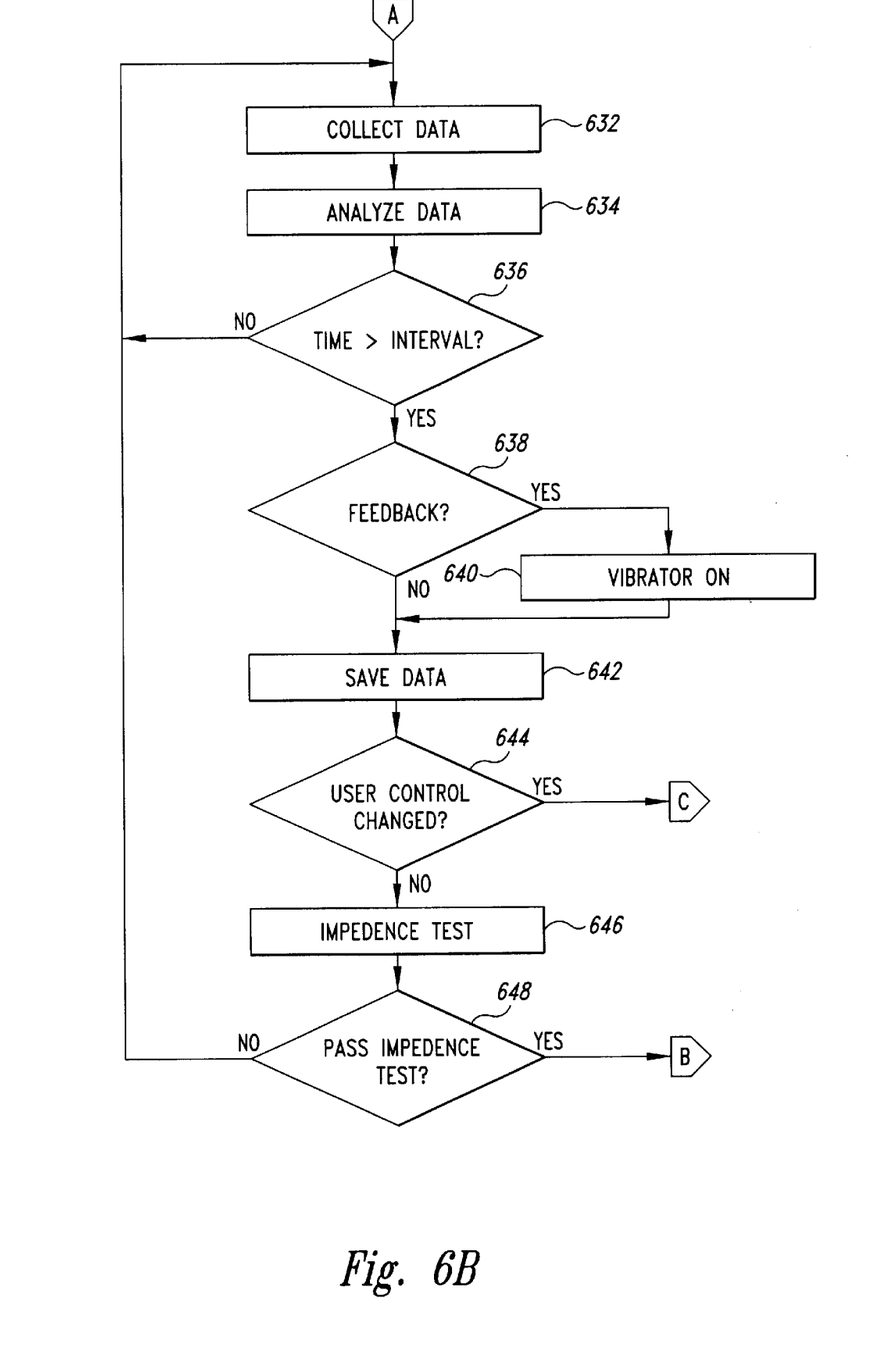

In the depicted embodiment, a procedure implemented in the microcontroller 524 of the HRV feedback monitor 110 to monitor heart rate variability of the user 140 and provide appropriate feedback is illustrated in FIGS. 6A and 6B. The procedure starts at step 610 and proceeds on to sleep mode 612. In the sleep mode 612, the HRV feedback monitor 110 requires minimal amount of power from the battery 526. Little measurement and analysis activity is done in this sleep mode 612 by the HRV feedback monitor 110 except for periodic tests to determine whether the HRV feedback monitor should switch to an operational mode. These periodic tests are indicated by decision step 614 where the HRV feedback monitor 110 determines whether it should switch from the sleep mode 612 to an operational mode. In decision step 614, if a signal such as a reset signal or an interrupt signal is received by the microcontroller 524, the microcontroller switches from sleep mode 612 into an operational mode. For instance, if the microcontroller 524 is reset, this would also cause the microcontroller to switch into an operational mode. A watchdog timer also is part of the microcontroller 524 in which after a preset time the controller resets which would also put the HRV feedback monitor 110 into an operational mode. Also, during the decision step 614, impedance levels of the electrodes 510–516 are measured and compared with a threshold by the microcontroller 524. This threshold level is typically 2 mega ohms for impedance and is measured with a small AC current being applied to the electrodes with resulting voltage being measured. If the impedance level drops below the threshold level, the HRV feedback monitor switches from sleep mode 612 into the operational mode.

Once the microcontroller 524 determines to switch from the sleep mode 612 to an operational mode, the procedure branches under the "yes" condition of decision step 614 to step 616. If no conditions presently exist to cause the HRV feedback monitor 110 to switch from sleep mode 612 into operational mode, the decision step 614 branches under the "no" condition back to the sleep step 612. The decision step 614 is repeated periodically until the decision step 614 branches under the "yes" condition to step 616. In step 616, the status and power indicators 460 and 462 (being red and green lights in the depicted embodiment) are flashed.

The procedure goes on to step 618 where self tests are performed by the HRV feedback monitor 110. These self tests include another impedance measurement of the electrodes 510–516 using a threshold typically different than the wake up threshold used for impedance measurement of the decision step 614. The impedance tests of the electrodes 510–516 in step 618 indicate, among other things, whether the electrodes 510–516 are in place. The electrode impedance test of step 618 is also used to determine if the impedance of each signal electrode 510 and 512 with respect to ground is too high for proper operation at the HRV signal levels to be monitored. This test threshold is a programmable variable. It is measured the same as the "power on" impedance test used in determination step 614 but the impedance threshold is typically lower than the threshold used for the "power on" impedance test. Consequently, a short period of time may be required for the skin to absorb a sufficient amount of conductive cream to reach this lower impedance threshold. Use of conductive cream with electrodes level is well known in the art. A typical threshold level for impedance is below 2 mega ohms for detection while the device is in use. As stated, the HRV signal measured is in the microvolt range with a frequency of between 20 and 400 Hz. The operating impedance should have little effect on measurement of heart rate variability once it is within an acceptably low level. A high impedance on the other hand results in masking the lower levels of the HRV signals with noise.

A calibration test is included in the self tests of step 618. The calibration test involves a 200 microvolt AC test signal switched to the electrode inputs and furnished to the A to D converter 522 as an HRV signal to bc measured. The A to D converter 522 converts the analog signal to a digital signal and the measured value of the digital signal is compared by the microcontroller 524 to stored high and low limits which are typically plus or minus 5% of the applied 200 microvolt AC signal. If the measured value of the applied test signal is outside the stored high and low limits, the impedance test fails, otherwise, the impedance test passes. The criteria for passing varies among the other embodiments depending on the desired accuracy level of the electrodes.

Another self-test of step 618 tests a common mode rejection (CMR). Both of the signal electrodes 510 and 512 are switched to a same high level input signal, typically 1 volt AC. A resultant measured value is then compared by the microcontroller 524 to a stored high limit which is typically 1 microvolt. Any voltage difference out of the input amplifier 518 greater than this 1 microvolt test limit results in a failed CMR test. However, if the voltage difference output from the input amplifier 518 is below the 1 microvolt test limit, the CMR test is passed.

The self-tests of step 618 also include a self-noise test where both electrode inputs of the signal electrodes 510 and 512 are switched to ground. Tile measured signal value is compared to a stored high limit, typically 1 microvolt, which if exceeded, fails the test; otherwise it passes the test. Also, in the depicted embodiment, the self-tests of step 618 also include a battery test that measures voltage out of the battery 526 to determine whether there is sufficient power stored in the battery.

After all the tests are performed in step 618 the procedure moves to decision step 620 where the microcontroller 524 determines whether or not a time out has occurred. The time value typically for a time out is between 1 and 15 minutes. If a time out has occurred, decision step 620 branches under the "yes" condition to step 622 where both red light status indicator 460 and green light power indicator 462 are turned off. After step 622, the procedure goes back to the sleep mode of step 612. If a time out has not occurred, the procedure branches under the "no" condition of decision step 620 to decision step 624 to determine whether all the tests have been passed that were performed in step 618.

If not all tests of step 618 have been passed, the procedure branches under the "no" condition of the decision step 624 to step 626 to signal the user 140 via the red light status indicator 460 regarding the failed test. In the depicted embodiment, the red light status indicator is flashed to signal the user 140 and the green light power indicator 462 is turned off in step 626, which then goes back to step 618 wherein tests are further performed. If all tests of step 618 are passed, the procedure under step 624 branches under the "yes" condition to step 628 where the red light status indicator 460 and green light power indicator 462 are set to signal the user 140 that the HRV feedback monitor 110 is in operational condition. In the depicted embodiment, the user 140 is signaled with the red light status indicator 460 turned off and the green light power indicator slowly blinking. The green light continues to blink as long as the HRV feedback monitor 110 is in operational mode.

Step 628 then goes to step 630 where initialization is performed by the microcontroller 524 of the HRV feedback monitor 110. In the initialization step 630, the microcontroller 524 enters a ready status to begin collecting, analyzing, and storing data based on stored instructions related to the particular settings of the user control knob 450.

After initialization in step 630 the procedure moves to step 632 wherein electrical signal data is collected of the user's beating heart with the use of the electrodes 510–516, input amplifier 518, low pass filter 520 and A to D converter 522. The microcontroller 524 then performs digital filtering based on standard algorithms known in the art. The digital filtering rejects power line interference typically at 60 Hz and mechanical motion and vibration which is typically lower than 80 Hz. After collecting data in step 632 the HRV feedback monitor 110 goes onto step 634 where the data is analyzed to determine HRV levels as discussed above.

After the data is analyzed in step 634 the procedure goes to decision step 636 to determine whether the time since the last feedback event is greater than a predetermined interval. If the time is not greater than the predetermined interval, the decision step 636 branches under the "no" condition back to step 632 where more data is collected. If the time since the last feedback event is greater than the predetermined interval, the decision step 636 branches under the "yes" condition to decision step 638. In decision step 638, the microcontroller 524 of the HRV feedback monitor 110 determines whether the set of parameters related to feedback chosen via the user control knob 450 or downloaded from computer system 220 have been satisfied. These parameters including those discussed above are stored in data memory 529.

Depending on what set of parameters the user 140 has selected, the microcontroller 524 will then determine whether feedback is appropriate. If feedback is appropriate, decision step 638 branches under the "yes" condition to step 640 where the vibrator-motor 530 is activated to send a vibration signal to the user 140. After a predetermined time the vibrator-motor 530 is turned off and step 640 goes to step 642. If feedback is inappropriate, then decision step 638 branches under the "no" condition to step 642 wherein data is saved to data memory 529. In step 642 data is saved based on the current set of parameters chosen by the user 140 through the user control knob 450 and also based on what sets of parameters are downloaded into the HRV feedback monitor 110 by a therapist using computer system 220 tied to the HRV feedback monitor 110 through computer interface cable 230. The data saved would typically be the same as the results of the analysis performed in step 634 on the HRV signals.

After data is saved in step 642, the procedure goes to decision step 644 to determine whether or not the user 140 has selected another set of parameters with user control knob 450. If the user 140 has selected a different set of parameters to be implemented by the HRV feedback monitor 110, the procedure branches under the "yes" condition back to step 630 where initialization is again performed. If the user 140 has not changed to another set of parameters, the decision step 644 branches under the "no" condition to step 646 where another impedance test is performed. The impedance test in step 646 is the same as the impedance test performed in the self-tests of step 618. The impedance test is performed again in step 646 to ensure that the condition of the electrodes is still acceptable. After the impedance test is performed in step 646, the procedure goes to decision step 648 to determine whether the impedance test has been passed. If the impedance test has been passed, the decision step 648 branches under the "yes" condition back to step 632 where more HRV signal data is collected. If the impedance test performed in step 646 is not passed, decision step 648 branches under the "no" condition back to step 612 where the HRV feedback monitor 110 switches back to the sleep mode.

Figure 7:
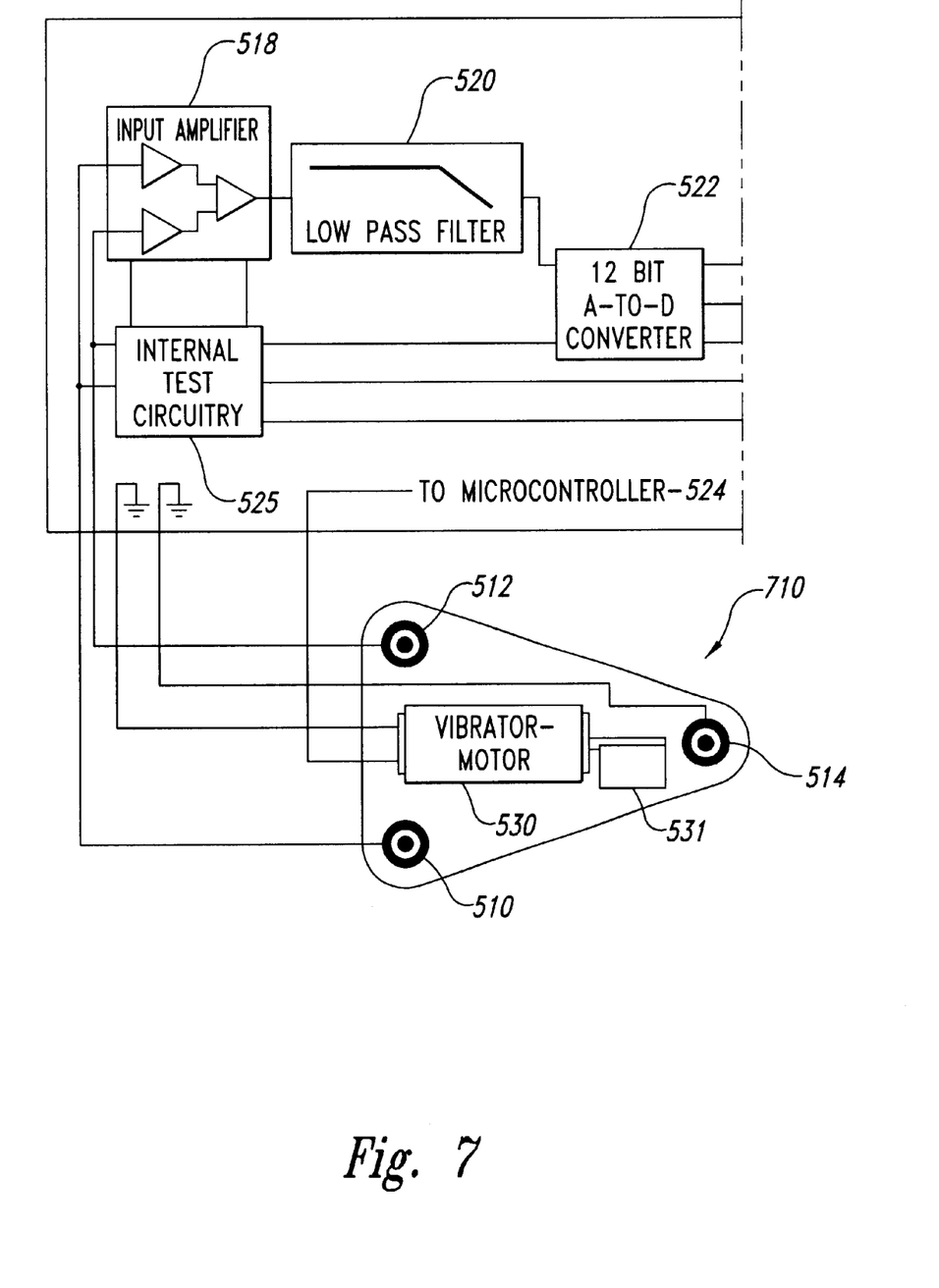
FIG. 7 is a block diagram showing detail of a sensor/feedback package of an alternative embodiment of the invention of FIG. 1.

In an alternate embodiment, the vibrator-motor 530 and weight 531 are located with the electrodes 510, 512, and 514 in a sensor/feedback package 710. The sensor/feedback package 710 is separate from the housing 120 of the HRV feedback monitor 110 as shown in FIG. 7. The housing 120 still contains all the other components of the HRV feedback 110 previously discussed. The electrodes 510, 512, and 514 and the vibrator-motor 530 are still electrically connected to the same components of the HRV feedback monitor 110. The signal electrodes 510 and 512 are connected to the input amplifier 518. The ground electrode 514 is connected to a common ground of the HRV feedback monitor 110. The vibrator-motor 530 is connected to the microcontroller 524 and ground. In this case, the electronic connections are provided through an external electrical cable. The rest of the HRV feedback monitor 110 including the housing 120 is still worn by the user 140 in a location other than the monitored location.

The sensor/feedback package 710 is used to locate the electrodes 510–514 in regions of the body of the user 140 when comfort issues would exclude placement of the housing 120 of the HRV feedback monitor 110. Since the vibrator-motor 530 and weight 531 are co-located with the electrodes 510–514, tactile feedback is still administered to the monitored region of the body of the user 140. Applying tactile feedback to the monitored region through the sensor/feedback package 710 maintains the direct association between feedback and the condition being monitored even when the housing 120 is located in a region of the body of the user 140 other than the monitored region.

Figure 8A:
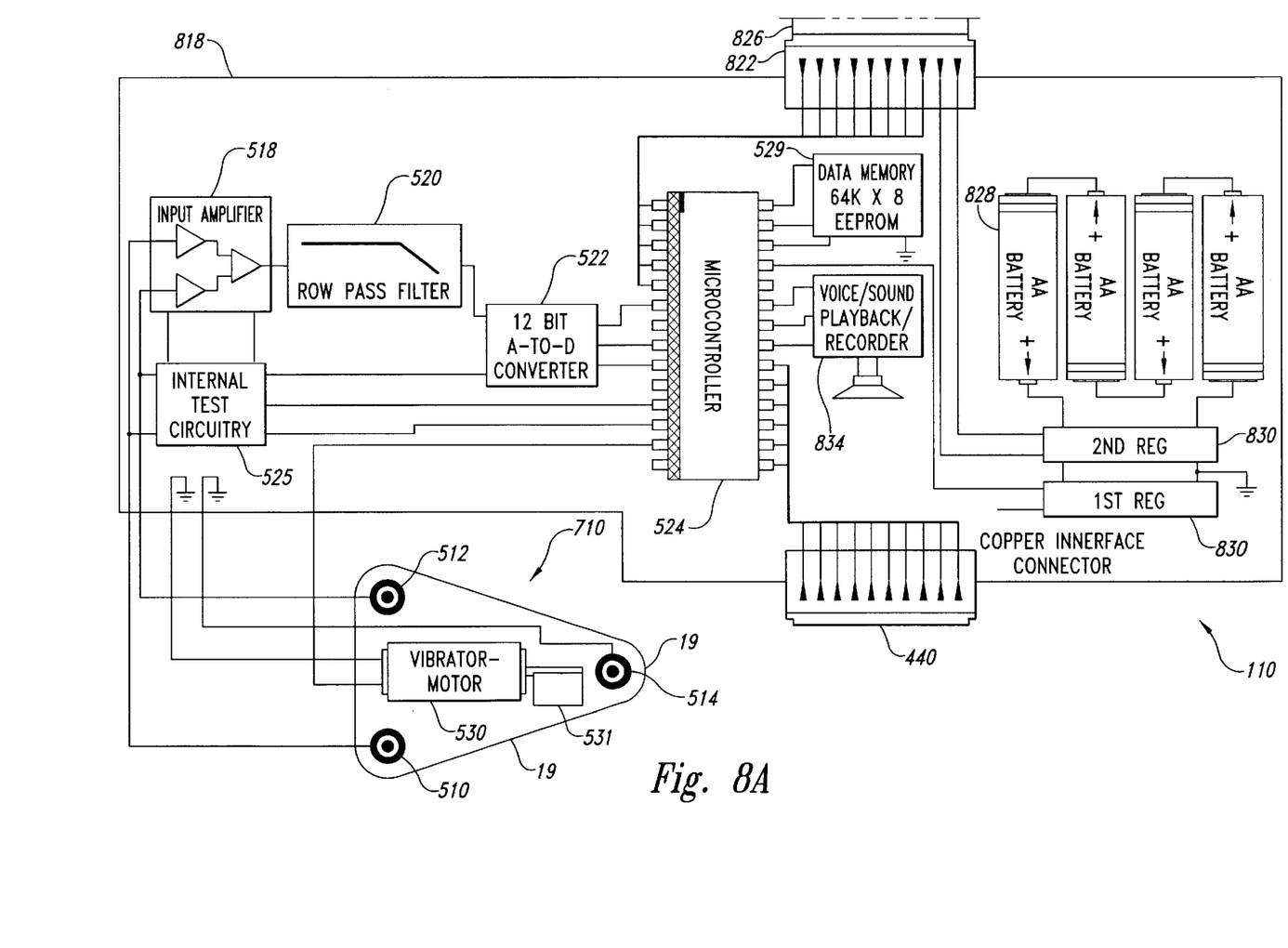
FIGS. 8A and 8B is a block diagram of an alternative embodiment of the invention of FIG. 1.
Figure 8B:
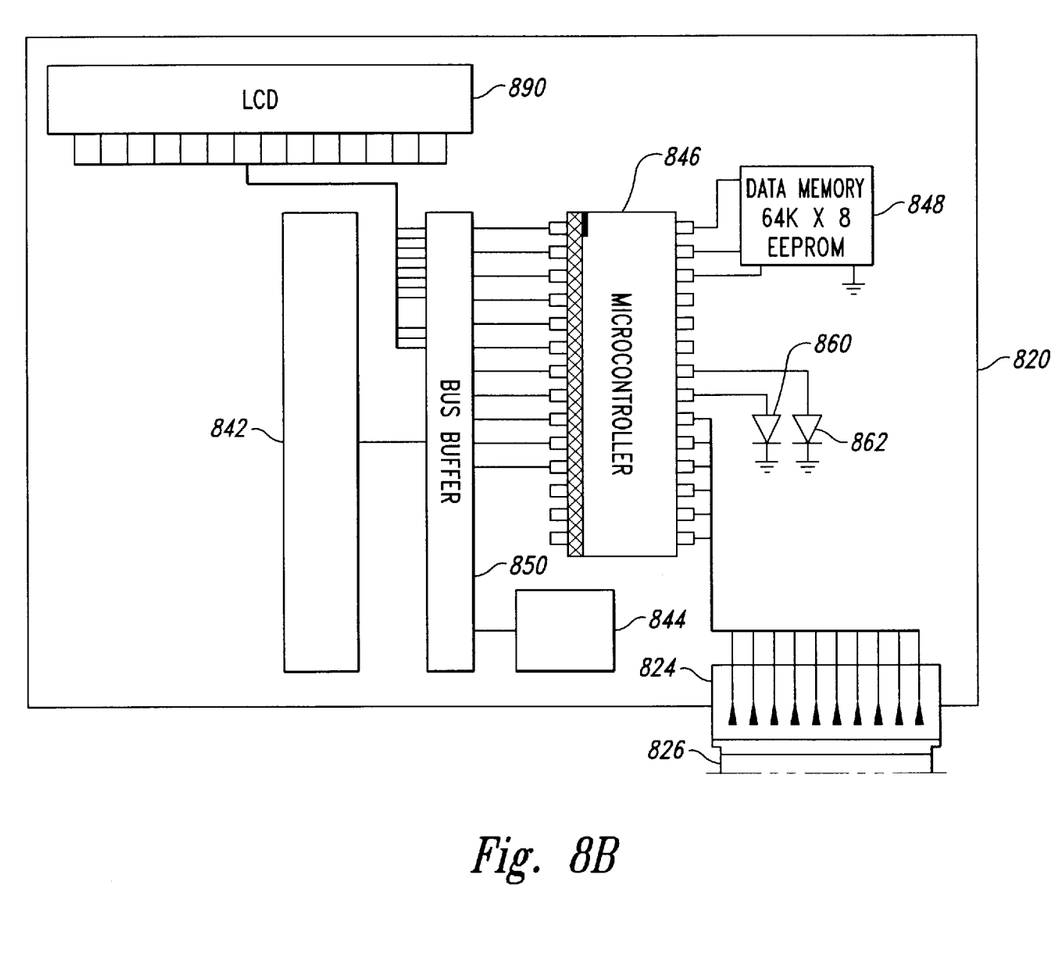

In another embodiment, visual and audio feedback is provided in addition to tactile feedback. In this embodiment, as shown in FIGS. 8A and 8B, the HRV feedback monitor 110 is divided into three sections: the sensor/feedback package 710, the master module 818, and the slave module 820. The master module 818 is connected to the slave module 820 via master connector 822, slave connector 824, and master-slave connector cable 826 as shown in FIGS. 8A and 8B. The master module 818 has most of the components of the HRV feedback monitor 110 except that in this case, the master module has a larger capacity power source 828, a first regulator 830 to regulate power to the microcontroller 524 and a second power regulator 832 to regulate power to the slave module 820. In addition, the master module 818 also includes a voice/sound playback/recorder 834. The audio output of the voice/sound playback/recorder 834 indicates surface HRV activity either by predefined tones or prerecorded voice. The prerecorded voice provides additional feedback in that voice prompts can be used to instruct the user regarding their behavior and operation of the HRV feedback monitor 110. The voice/sound playback/recorder 834 is also used to record tones or voice prompts.

The slave module 820 includes an LCD display 840 and a bar graph 842 which supply text and visual feedback, respectively, to the user 140. A keyboard 844 allows the user 140 to input commands or query the HRV feedback monitor 110. A microcontroller 846 located in the slave module 820 handles processing of the display outputs and keyboard inputs. A memory storage device 848 is connected to the microcontroller to store data and instructions used by the microcontroller. A red light status indicator 860 and a green light power indicator 862 are also located in the slave module 820.

The configuration shown in FIGS. 8A and 8B allows flexibility of use in that the sensor/feedback package 710, the master module 818 and slave module 820 can be located in separate regions on the user 140. For instance, the sensor/feedback package 710 can be located on a region of the user 140 to be monitored. The master module 818 can be worn on the user 140 in a location other than the monitored region to allow for better fit and greater comfort. The slave module 820 can be either worn by the user 140 or located somewhere else such as on a table top. In this alternate embodiment, the visual feedback and keyboard input is optional so that the user 140 also monitors HRV activity level without the slave module 820. In another alternative embodiment, the master module 818 and slave module 820 communicate with one another via a wireless communication link.

All of the above U.S. patents, applications and articles are incorporated by reference. While the depicted embodiment is used in training and rehabilitation for fitness levels and health conditions, other embodiments of the invention can be similarly used for monitoring and providing feedback related to other objectives, such as, for example, sports related activities, scientific research, or business activities. Furthermore, aspects of the embodiments disclosed in the commonly assigned, concurrently filed and co-pending U.S. applications referenced above can be combined with aspects of the embodiments disclosed herein. For instance, aspects of the Respiration Feedback Monitor system could be combined with aspects disclosed herein resulting in a feedback monitor for a user's respiration and heart activities.

As an alternative example, aspects of the Electromyographic Feedback Monitor System could be combined with aspects disclosed herein resulting in a feedback monitor for a user's muscle and heart activities.

These and other changes can be made to the invention in light of the above-detailed description. In general, in the following claims, the terms should not be construed to limit the invention to specific embodiments disclosed in the specification and the claims, but should be construed to include all HRV feedback monitors that operate under the claims to provide a system for monitoring and providing appropriate feedback related to HRV activity of a user. Accordingly, the invention is not limited by the disclosure, but instead its scope is to be determined entirely by the following claims.

What is claimed is:

1. A heart rate variability feedback system for a user, the system comprising:
    an output device configured to transmit a sensory signal perceptible by the user based on the output device receiving an activation signal;
    a plurality of electrodes configured to produce electrical signals based on electrical activity of the user's heart;
    a housing sized and configured to be worn by the user;
    a memory housed by the housing wherein the memory is configured to store heart rate variability feedback criteria associated with a plurality of operational modes;
    a mode selection device housed by the housing and configured to be operated by the user to select any one of the plurality of operational modes as a selected operational mode; and
    a processor housed by the housing and coupled to the plurality of electrodes, the output device, and the memory, the processor configured to receive digital signals associated with the electrical signals produced by the electrodes, the processor configured to determine heart rate variability of the user based on the digital signals and to transmit an activation signal to the output device based on whether the determined heart rate variability satisfies the heart rate variability feedback criteria associated with the selected operational mode.

2. The heart rate variability feedback system of claim 1 wherein the plurality of operational modes comprises: Percent Time Amplitude Mode, Threshold Amplitude Mode, Median Frequency Mode, Prompted Exercise Mode, or Threshold Shaping Mode.

3. The heart rate variability feedback system of claim 1, further comprising:
    a connector configured to detachably connect the heart rate variability feedback system to a computer system via an interface cable for transmission of data including heart rate variability data and criteria.

4. A heart rate variability feedback system for a user, the system comprising
    an output device configured to transmit a sensory signal perceptible by the user based on the output device receiving an activation signal;
    a plurality of electrodes configured to produce electrical signals based on electrical activity of the user's heart;
    a housing sized and configured to be worn by the user;
    a memory housed by the housing wherein the memory is configured to store heart rate variability feedback criteria; and
    a processor housed by the housing and coupled to the plurality of electrodes, the output device, and the memory, the processor configured to receive digital signals associated with the electrical signals produced by the electrodes, the processor configured to determine a measured heart rate variability of the user based on the digital signals and to transmit the activation signal to the output device based on whether the measured heart rate variability satisfies the heart rate variability feedback criteria, the processor configured to modify the heart rate variability feedback criteria based on the measured heart rate variability.

5. The heart rate variability feedback system of claim 4 wherein the memory is further configured to store a goal threshold associated with the heart rate variability feedback criteria and wherein the processor is further configured to adjust a median threshold toward the goal threshold if the measured heart rate variability satisfies the median threshold and to transmit the activation signal to activate the output device if the measured heart rate variability does not satisfy the median threshold.

6. The heart rate variability feedback system of claim 4 wherein the memory is further configured to store heart rate variability data as stored heart rate variability data and wherein the processor is further configured to determine a trend based on the stored heart rate variability data and to modify the heart rate variability feedback criteria base on the trend.

7. The heart rate variability feedback system of claim 4 wherein the memory is further configured to store previously measured heart rate variability as stored heart rate variability data and wherein the processor is further configured to determine a trend based on the stored heart rate variability data and the measured heart rate variability and to adjust the activation signal to subsequently adjust the sensory signal based on the trend.

8. The heart rate variability feedback system of claim 4 wherein the heart rate variability feedback criteria and determined heart rate variability are associated with time domain or frequency domain calculations associated with the electrical signals produced by the electrodes.

9. A heart rate variability feedback system for a user, the system comprising:
    a sensor package sized and configured to be worn by the user;
    a plurality of electrodes affixed to the sensor package, the electrodes configured to produce electrical signals based on electrical activity of the user's heart, each of the plurality of electrodes being located substantially along a periphery of a first area of the sensor package;
    a vibration output device affixed to the sensor package, the vibration output device configured to transmit a vibration signal perceptible by the user based on the vibration output device receiving an activation signal, the vibration output device substantially located centrally in the first area of the sensor package;
    a housing sized and configured to be worn by the user;
    a memory housed by the housing wherein the memory is configured to store heart rate variability feedback criteria; and a processor housed by the housing and coupled to the plurality of electrodes, the vibration output device and the memory, the processor configured to receive digital signals associated with the electrical signals produced by the electrodes, the processor configured to determine heart rate variability of the user based on the digital signals and to transmit the activation signal to the vibration output based on whether the determined heart rate variability satisfies the heart rate variability feedback criteria.

10. The heart rate variability feedback system of claim 9 wherein the sensor package is an integral part of the housing.

11. The heart rate variability feedback system of claim 9, further including:
- an electrical cable external to the housing wherein electrical signals produced by the electrodes are sent from the sensor package to the housing by the electrical cable; and
- a slave output electrically coupled to the processor by an electrical cable external to the housing.

12. The heart rate variability feedback system of claim 9, further including:
- an electrical cable external to the housing wherein electrical signals produced by the electrodes are sent from the sensor package to the housing by the electrical cable; and
- a slave output electrically coupled to the processor by a wireless communication link.

13. A heart rate variability feedback system for a user, the system comprising:
- an vibratory output device configured to transmit a vibratory signal to the user subsequent to the vibratory output device receiving an activation signal;
- a plurality of electrodes configured to produce electrical signals based on electrical activity of the user's heart;
- a housing sized and configured to be worn by the user;
- a memory housed by the housing wherein the memory is configured to store heart rate variability feedback criteria; and
- a processor housed by the housing and coupled to the plurality of electrodes, the output device, and the memory, the processor configured to receive digital signals associated with the electrical signals produced by the electrodes, the processor configured to determine a measured heart rate variability of the user based on the digital signals and to transit the activation signal to the vibratory output device based on a comparison of the measured heart rate variability with the heart rate variability feedback criteria, the processor configured to control the duration of the vibratory signal to be directly related to a difference between tile measured heart rate variability and a threshold of the heart rate variability feedback criteria.

14. The heart rate variability feedback system of claim 13, wherein the electrodes are integrally affixed to the housing.

15. The heart rate variability feedback system of claim 13 wherein the processor is configured to analyze the digital signals regarding a distribution associated with a time or frequency domain.

16. A heart rate variability feedback system for a user, the system comprising:
- a output device configured to transmit a prerecorded verbal instruction perceptible by the user based on the output device receiving an activation signal;
- a plurality of electrodes configured to produce electrical signals based on electrical activity of the user's heart;
- a housing sized and configured to be worn by the user;
- a memory housed by the housing wherein the memory is configured to store heart rate variability feedback criteria and prerecorded verbal instructions; and
- a processor housed by to the housing and coupled to the plurality of electrodes, the output device, and the memory, the processor configured to receive digital signals associated with the electrical signals produced by the electrodes, the processor configured to determine a measured heart rate variability of the user based on the digital signals and to transmit the activation signal to the output device based on whether the measured heart rate variability satisfies the heart rate variability feedback criteria, the processor configured to select the prerecorded verbal instruction based upon comparison of the heart rate variability feedback criteria with the measured heart rate variability.

17. A heart rate variability feedback system for a user, the system comprising:
- a output device configured to transmit a sensory signal perceptible by the user based on the output device receiving an activation signal;
- a plurality of electrodes configured to produce electrical signals based on electrical activity of the user's heart;
- a housing sized and configured to be worn by the user;
- a memory housed by the housing wherein the memory is configured to store heart rate variability feedback criteria and prerecorded verbal instructions; and
- a processor housed by to the housing and coupled to the plurality of electrodes, the output device, and the memory, the processor configured to receive digital signals associated with the electrical signals produced by the electrodes, the processor configured to transmit a first processor signal as the activation signal for the output device to transmit a first output signal as the sensory signal, the processor configured to determine a measured heart rate variability of the user based on the digital signals subsequent to transmitting the first processor signal and to transmit a second processor signal as the activation signal to the output device to transmit a second output signal as the sensory signal based on or more of the following: whether the measured heart rate variability satisfies the heart rate variability feedback criteria and passage of a period of time subsequent to transmitting the first processor signal.

18. The heart rate variability feedback system of claim 17 wherein the first output signal is configured to signal the user to begin exercising and the second output signal is configured to signal the user to stop exercising.

19. The heart rate variability feedback system of claim 17 wherein the processor and memory are monolithically integrated on the same integrated circuit.

20. The heart rate variability feedback system of claim 17 wherein the output device emits audio tones or voice prompts.

21. A heart rate variability feedback system for a user, the system comprising:
- a plurality of electrodes configured to produce electrical signals based on electrical activity of the user's heart;
- a housing sized and configured to be worn by the user;
- a memory housed by the housing wherein the memory is configured to store heart rate variability feedback criteria and prerecorded verbal instructions; and
- a processor housed by the housing and coupled to the plurality of electrodes, the output device, and the memory, the processor configured to receive digital signals associated with the electrical signals produced by the electrodes, the processor while operating in an operational mode configured to determine a measured heart rate variability of the user based on the digital signals and while in a sleep mode configured to conserve power, the processor configured to determine measured impedance levels of the plurality of electrodes and to select between operating in the operation mode and the sleep mode based upon the measured impedance levels of the plurality of electrodes.

22. A heart rate variability feedback system for a user, the system comprising:

a plurality of electrodes configured to produce electrical signals based on electrical activity of the user's heart;

a housing sized and configured to be worn by the user;

a memory housed by the housing wherein the memory is configured to store heart rate variability feedback criteria and prerecorded verbal instructions; and a processor housed by the housing and coupled to the plurality of electrodes, the output device, and the memory, the processor configured to receive digital signals associated with the electrical signals produced by the electrodes, the processor configured to determine a measured heart rate variability of the user based on the digital signals, the processor configured to perform fault detection comprising calibration of the electrodes, determining common mode rejection of a differential amplifier, and determining self-noise of the heart rate variability feedback system.

23. A method to be implemented by a heart rate variability feedback system to be worn by a user, the method comprising:

locating sensors substantially along a periphery of a first area;

locating a vibratory output device substantially centrally in the first area, the vibratory output device configured to generate vibrations subsequent to receiving an activation signal, the vibrations to be perceived by the user;

measuring electrical signals associated with electrical activity of the user's heart;

determining a measured heart rate variability based on the electrical signals;

determining an analysis of the measured heart rate variability with respect to heart rate variability criteria; and transmitting the activation signal to the vibratory output based upon the analysis.

24. A method to be implemented by a heart rate variability feedback system to be worn by a user, the method comprising:

storing heart rate variability feedback criteria associated with a plurality of operational modes;

providing selection to the user of the plurality of operational modes for designation by the user of a selected mode;

measuring electrical signals associated with electrical activity of the user's heart;

determining a measured heart rate variability based on the electrical signals;

determining an analysis of the measured heart rate variability with respect to heart rate variability criteria of the selected mode; and transmitting a sensory output to the user based upon the analysis.

25. A method to be implemented by a heart rate variability feedback system to be worn by a user, the method comprising:

storing heart rate variability feedback criteria as a stored heart rate variability feedback criteria;

measuring electrical signals associated with electrical activity of the user's heart;

determining a measured heart rate variability based on the electrical signals;

determining an analysis of the measured heart rate variability with respect to the stored heart rate variability criteria;

transmitting a sensory output to the user based upon the analysis;

modifying the stored heart rate variability feedback criteria as a modified heart rate variability feedback criteria based upon the analysis; and storing the modified heart rate variability feedback criteria as the stored heart rate variability feedback criteria.

* * * * *

UNITED STATES PATENT AND TRADEMARK OFFICE
CERTIFICATE OF CORRECTION

PATENT NO. : 6,212,427 B1
DATED : April 3, 2001
INVENTOR(S) : Jan C. Hoover

It is certified that error appears in the above-identified patent and that said Letters Patent is hereby corrected as shown below:

Claim 4, column 15,
Line 64, "system comprising" should read -- system comprising --.

Claim 13, column 17,
Line 52, "between tile measured" should read -- between the measured --.

Signed and Sealed this

Twenty-third Day of October, 2001

Attest:

NICHOLAS P. GODICI
Attesting Officer  Acting Director of the United States Patent and Trademark Office